Figure 1:
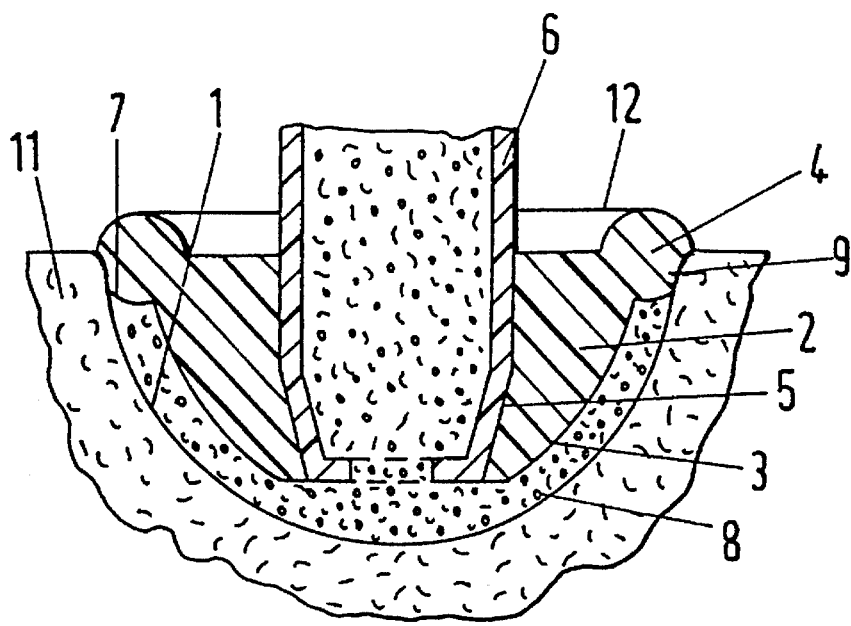

United States Patent

Willert et al.

Patent Number: 5,501,687
Date of Patent: Mar. 26, 1996

[54] BODY FOR DISTRIBUTING BONE CEMENT FOR THE ANCHORING OF IMPLANTS

[75] Inventors: Hans-Georg Willert, Götingen, Germany; Kurt Bider, Winterthur, Switzerland

[73] Assignee: Sulzer Medizinaltechnik AG, Winterthur, Switzerland

[21] Appl. No.: 148,767

[22] Filed: Nov. 4, 1993

[30] Foreign Application Priority Data

Nov. 20, 1992 [EP] European Pat. Off. .............. 92810905

[51] Int. Cl.⁶ ................................ A61B 17/88; A61F 2/34
[52] U.S. Cl. .................................. 606/94; 606/92; 623/22
[58] Field of Search .......................... 606/92–94; 623/19, 623/22

[56] References Cited

U.S. PATENT DOCUMENTS

| | | | |
|---|---|---|---|
| 3,866,248 | 2/1975 | Kummer | 606/92 |
| 4,274,163 | 6/1981 | Malcom et al. | 623/18 X |
| 4,399,814 | 8/1983 | Pratt et al. | 606/94 |
| 4,488,549 | 12/1984 | Lee et al. | 606/94 |
| 4,815,454 | 3/1989 | Dozier | 606/94 |
| 4,892,550 | 1/1990 | Huebsch | 623/22 |
| 4,896,662 | 1/1990 | Noble | 606/94 |
| 5,078,746 | 1/1992 | Garner | 623/16 |
| 5,116,377 | 5/1992 | Skripitz et al. | 623/23 |

*Primary Examiner*—David H. Willse
*Attorney, Agent, or Firm*—Townsend and Townsend and Crew

[57] ABSTRACT

A body (2) for distributing bone cement (8) rests by an elastic collar (4) against the outer edge of a hollow (1) in the bone and has a passage (5) through into the hollow (1) in the bone, into which a syringe (6) for bone cement may be inserted. In the hollow (1) in the bone the body (2) is made as a displacement body of the shape (3) of the implant which is to be inserted later. During injection into the space between the body and the hollow in the bone a designed pressure is maintained until the viscosity of the bone cement (8) is adequate for taking the body (2) out of the hollow (1) in the bone without bone cement (8) flowing back. Subsequently the actual implant may be pressed into the thus prepared but still plastically deformable countermould of bone cement (8).

6 Claims, 2 Drawing Sheets

BODY FOR DISTRIBUTING BONE CEMENT FOR THE ANCHORING OF IMPLANTS

The invention deals with a body for distributing bone cement for the anchoring of implants in a prepared hollow in bone corresponding with the outer geometry of the implant, as well as an associated method.

From the patent CH 639549 a cap is known which may be mounted on a cement syringe and ends in an elastic conical mouthpiece for pressing against the outer edge of a hollow in the bone during injection of the cement. One disadvantage of this arrangement is that large amounts of the cement which sets in dependence upon time and heats up in dependence upon the amount, is moved into the hollow in the bone in order to achieve a compression and that subsequently upon inserting the implant still larger amounts of cement are forced out of the hollow in the bone into the surrounding field of operation. Another possibility consists in the employment of hollow implants with a distributor system which may be fed from outside as described in the patent U.S. Pat. No. 4,274,163. One disadvantage of this arrangement consists in that a weakening of the implant arises from the distributor system, that in relation to the relatively small cross-sections of passage long paths of flow arise with surfaces flowing together, and that the production of the implant becomes more costly through a distributor system integrated in that fashion.

The invention takes these circumstances into account. It has the problem, without impairment of the structure of the implant, of bringing the bone cement into its final position with respect to the hollow in the bone. It solves this problem by the characterizing portions as described in the following summaries:

- A body is provided for distributing bone cement for the anchoring of implants in a hollow prepared in a bone to correspond with the outer geometry of the implant, characterized in that the body exhibits a mould which is copied from the outer shape of an implant which is to be inserted, especially a hipjoint socket, the mould being provided at the edge with a collar which closes off the hollow in the bone, whilst the body exhibits a passage through to the volume so enclosed, against which a bone cement syringe may be fitted, and that the body consists at least in the region of the collar of an elastic plastics which fits tightly against the hollow in the bone in the region of the collar.
- A method of distributing bone cement in a hollow in a bone by a body is provided and is characterized in that in a first step the body which is copied from the outer shape of the implant which is to be inserted, is pressed by a collar against the hollow in the bone; in a second step bone cement is injected via a passage in the body and distributed under after-pressure well into the microstructure of the surface of the hollow in the bone; in a third step the body is removed from the hollow in the bone, the bone cement remaining preshaped in the hollow in the bone with a view to the actual implant; in a fourth step the actual implant is inserted in the hollow in the bone and the excess bone cement swelling out at the edge is removed; and in a fifth step the implant is held in an aligned position until the bone cement has set.

The invention has the advantage that large cross-sections are possible for feeding the space between the implant and the hollow in the bone, that only as much bone cement as is necessary for the setting and connection is introduced into the hollow in the bone, and that because of the large cross-sections of feed a designed application pressure may be maintained very exactly during filling of the hollow in the bone.

A body for distributing bone cement rests by an elastic collar against the outer edge of a hollow in the bone and has a passage through into the hollow in the bone, into which a syringe for bone cement may be inserted. In the hollow in the bone the body is made as a displacement body having the shape of the implant to be inserted later. During injection into the space between the body and the hollow in the bone a designed pressure is maintained until the viscosity of the bone cement is adequate for taking the body out of the hollow in the bone without bone cement flowing back. Subsequently the actual implant may be pressed into the thus prepared but still plastically deformable countermould of bone cement.

Figure 2:
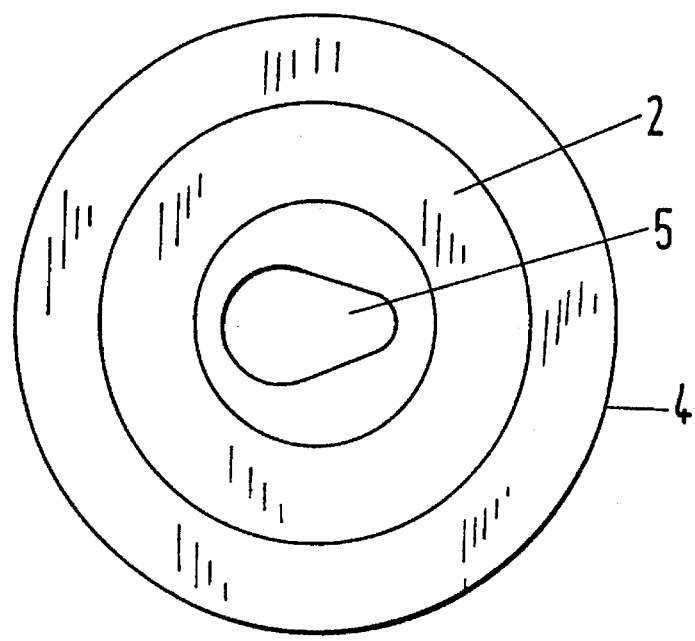
Figure 3:
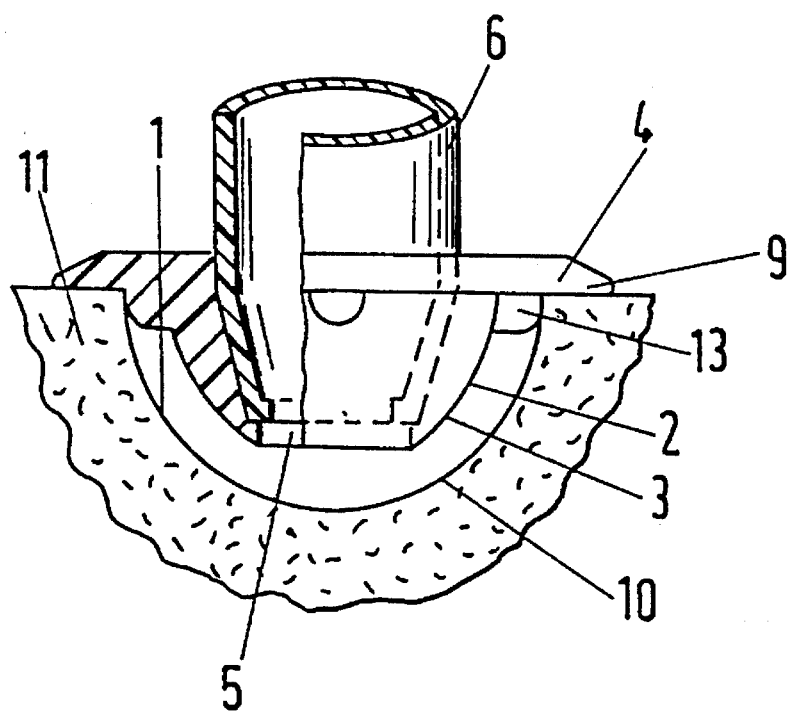
Figure 4:
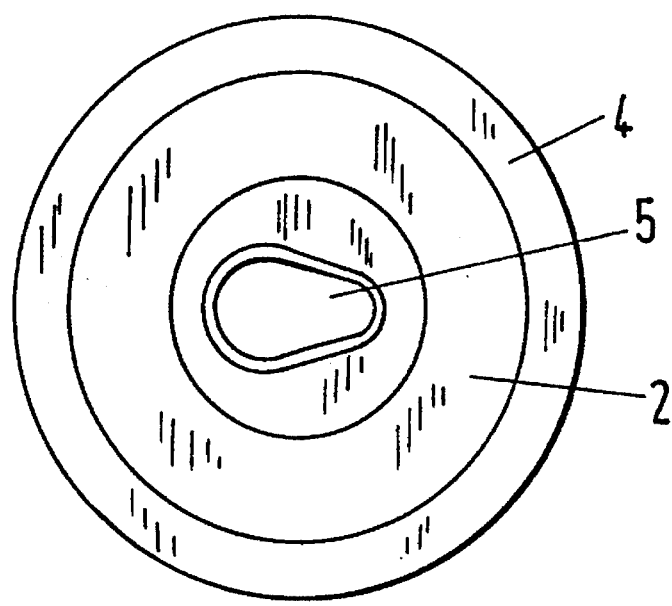

Advantageous further developments of the invention are set forth as follows. In one aspect, the body is characterized in that at high temperature the plastics is sufficiently stable to be able to be sterilized by the steam at 134° C. In another aspect, the body is characterized in that at least its surface in the region of the collar consists of silicone rubber. In a further aspect, the body is wetted with a release agent. In yet a further aspect, the release agent comprises a sterile physiological cooking-salt solution. The invention is described below with the aid of embodiments. There is shown in:

FIG. 1—a longitudinal section through a body designed for a hip joint socket and inserted in a hollow in a bone, after the injection of bone cement;

FIG. 2—a plan of the body in FIG. 1;

FIG. 3—a longitudinal section corresponding with the arrangement in FIG. 1 before the injection of bone cement, in which the body rests by a collar against the endface of the hollow in the bone and is centred by lugs inside the hollow in the bone; and FIG. 4—a plan of the body in FIG. 3.

In FIGS. 1 and 2 a body 2 with a collar 4 in the form of a bead 12 of elastic plastics 7 such, for example, as silicone rubber 9, rests against the edge of a hollow 1 in the bone. The mould 3 projecting into the hollow 1 in the bone corresponds in shape with that of a hip joint socket which is to be inserted later. The body 2 has a passage 5 against which a bone cement syringe 6 is pressed in order to compensate the hydrostatic upthrust while bone cement 8 is being pressed in. Through the large cross-section of passage 5 and the short paths of flow scarcely any loss of pressure results until the bone cement has reached the space between the mould 3 and the hollow 1 in the bone.

A pressure deemed an optimum at which the bone tissue 11 in the hollow 1 in the bone does not become overcharged with bone cement 8, may be maintained very exactly. When in accordance with the time pattern the bone cement has reached a viscosity at which it no longer flows under gravity into thin layers such as into the space between the mould 3 and the hollow in the bone, the body 2 may be loosened. It has been found that in doing so a separating agent such, for example, as a physiological cooking-salt solution, is of advantage if it has been applied before the injection of the bone cement 8 into the body 2.

After the loosening of the mould 3 the actual implant is pressed into the still plastically deformable bone cement. Because of the fine microstructure of the bone tissue 11 and the now higher viscosity of the bone cement 8, overcharging of the former with bone cement is scarcely still possible.

The body 2 is reusable. But it must be sufficiently stable at high temperature to be able like, for example, silicone rubber, to be sterilized by steam at 134° C.

In FIG. 3 and 4 a body 2 for a hip joint socket is fitted to a prepared hollow 1 in the bone and by a collar 4 which projects sideways over the hollow in the bone, bears against the outer bone tissue. The sealing part of the collar 4 is coated with silicone rubber 4 in order to equalize unevennesses in the bone tissue. The sealing action is limited to the extent that enclosed air can escape during injection of the bone cement. For better centreing of the body 2 lugs 13 fitted below the collar 4, bear inside the hollow 1 in the bone against the bone tissue 11.

We claim:

1. A removable mold for distributing bone cement from a hand-held bone cement syringe and into a hip joint cavity prepared in a bone, the hip joint cavity for receiving and anchoring a hip joint implant, the mold for distributing the bone cement in the hip joint cavity so that the bone cement corresponds in shape with an outer geometry of the implant, the mold comprising:

a solid rubber-like body having a molding surface that is fashioned to correspond in shape to the outer geometry of the hip joint implant, and wherein the body defines a central channel, the channel being sized to receive and position the bone cement syringe near the molding surface to allow the hope cement to be delivered through the channel with minimal travel and with minimal loss of pressure so that the cement may be evenly distributed between the bone and the molding surface upon hand operation of the syringe; and wherein the mold further includes an elastic collar integrally formed about the periphery of the body, the collar being sized to rest against the bone and to hold the molding surface spaced-apart from the bone, and wherein the elasticity of the mold allows the mold to be removed from the hip joint cavity without substantial removal of the cement when the cement reaches a desired viscosity and the hip joint implant placed therein.

2. A mold as in claim 1, wherein the body is sufficiently stable to be able to be sterilized by steam at 134° C.

3. A mold as in claim 1, wherein the collar is constructed of silicone rubber.

4. A mold as in claim 1, further comprising a release agent for wetting the body.

5. A mold as in claim 4, wherein the release agent comprises a sterile physiological cooking-salt solution.

6. A hip joint implantation system for anchoring a hip joint implant into a hip joint cavity prepared in a bone, the system comprising:

a hand-held bone cement syringe for injecting bone cement; and a removable mold for receiving the bone cement syringe and for distributing the bone cement into the hip joint cavity so that the bone cement corresponds in shape with an outer geometry of the implant, the mold comprising:

a solid rubber-like body having a molding surface that is sized to correspond in shape to the outer geometry of the hip joint implant, and wherein the body defines a channel, the channel being sized to receive and position the bone cement syringe near the molding surface to allow the bone cement to be delivered through the channel with minimal travel and with minimal loss of pressure so that the cement may be evenly distributed between the bone and the molding surface upon hand operation of the syringe; and wherein the mold further includes an elastic collar integrally formed about the periphery of the body, the collar being sized to rest against the bone and to hold the molding surface spaced-apart from the bone, and wherein the elasticity of the mold allows the mold to be removed from the hip joint cavity without substantial removal of the cement when the cement reaches a determined viscosity and the hip joint implant placed therein.

* * * * *